United States Patent [19]

Ohara et al.

[11] Patent Number: 4,611,088
[45] Date of Patent: Sep. 9, 1986

[54] PROCESS FOR PREPARING D-α-(6-METHOXY-2-NAPHTYL) PROPIONIC ACID

[75] Inventors: Yoshio Ohara, Narashino; Kazutaka Arai, Yotsukaido; Yasuhiro Takahashi, Chiba; Yasuo Takakuwa, Funabashi, all of Japan

[73] Assignee: Nissan Chemical Industries, Ltd., Tokyo, Japan

[21] Appl. No.: 656,457

[22] Filed: Oct. 1, 1984

[30] Foreign Application Priority Data

Oct. 11, 1983 [JP] Japan ................. 58-189534

[51] Int. Cl.$^4$ .............................................. C07C 65/30
[52] U.S. Cl. ................................................... 562/466
[58] Field of Search ......................................... 562/466

[56] References Cited

U.S. PATENT DOCUMENTS

| 3,652,683 | 3/1972 | Harrison | 562/466 |
| 3,658,858 | 4/1972 | Harrison | 562/466 |
| 3,663,584 | 5/1972 | Alvarez | 562/466 |
| 3,694,476 | 9/1972 | Alvarez | 562/466 |
| 3,975,432 | 8/1976 | Alvarez | 562/466 |
| 4,328,356 | 5/1982 | Giordano et al. | 562/466 |

Primary Examiner—Paul J. Killos
Attorney, Agent, or Firm—Frishauf, Holtz, Goodman & Woodward

[57] ABSTRACT

A process for preparing d-α-(6-methoxy-2-naphthyl)-propionic acid, which comprises hydrolyzing an ester of d-α-(6-methoxy-2-naphthyl)propionic acid in an aqueous solution containing a basic catalyst.

15 Claims, No Drawings

PROCESS FOR PREPARING D-α-(6-METHOXY-2-NAPHTYL) PROPIONIC ACID

BACKGROUND OF THE INVENTION

This invention relates to a novel process for preparing d-α-(6-methoxy-2-naphthyl)propionic acid.

The d-α-(6-methoxy-2-naphthyl)propionic acid or its salt is useful as, for example, anti-flammatory or analgesic agents.

As processes for preparing d-α-(6-methoxy-2-naphthyl)-propionic acid, there have been heretofore known (i) a process in which aromatic modification of α-(6-methoxy-2-naphthyl)propionic acid is optionally resolved, (ii) a process in which an ester of d-α-(6-methoxy-2-naphthyl)-propionic acid is hydrolyzed in the presence of an acid catalyst, and the like.

The process in which racemic modification of α-(6-methoxy-2-naphthyl)propionic acid is optically resolved, however, can not be said to be a satisfactory one from an economical view point because it is necessary to repeat the crystallization several times or more and to use expensive agents for the optical resolution.

In the process in which an ester of d-α-(6-methoxy-2-naphthyl)propionic acid is hydrolyzed in the presence of an acid catalyst, the methoxy group at the 6-position in the naphthyl group of the carboxylic acid which is a desired product or of the unreacted starting ester tends to be partially converted to a hydroxy group by hydrolysis to form d-α-(6-hydroxy-2-naphthyl)propionic acid or its ester as a by-product, requiring treatment for purification after completion of the hydrolysis, and therefore the above process also can not be said to be a fully satisfactory one for an industrial application.

Further, there is known a process in which an ester of d-α-(6-methoxy-2-naphthyl)propionic acid is hydrolyzed in an organic solvent containing an alkali catalyst. In this process, however, racemization reaction occurs simultaneously with hydrolysis to result in remarkable decrease in the optical purity of the resulting product (see U.S. Pat. No. 4,417,070, Table 2 on page 4), and the process can be said not to be a good efficiency.

SUMMARY OF THE INVENTION

The present inventors have made extensive studies in order to eliminate the drawbacks in the processes described above, and as a result, have found that a process in which the hydrolysis is effected in an aqueous alkali (basic) catalyst solution is unexpectedly accompanied with little racemization reaction, and have accomplished this invention.

More specifically, in hydrolysing an ester such as the ester of d-α-(6-methoxy-2-naphthyl)propionic acid, which is hardly soluble in water, there have been usually used water-soluble organic solvents such as ethanol, methanol and the like, which are capable of dissolving the ester of d-α-(6-methoxy-2-naphthyl)propionic acid but do not participate in the reaction, in order to enhance the rate of reaction.

Opposed to the above, the present inventors have used water as a solvent, and as a result, have found that hydrolysis of the ester group unexpectedly proceeds while remarkably suppressing the racemization, and have accomplished this invention.

The present inventors have further found that in the present process there does not occur a side reaction that the methoxy group at the 6-position on the naphthyl group of the carboxylic acid or of the unreacted starting ester is converted to a hydroxy group by hydrolysis to form a by-product d-α-(6-hydroxy-2-naphthyl)propionic acid or its ester, whereas such a side reaction is observed in the acid-catalyzed hydrolysis as mentioned above.

Accordingly, this invention is to provide a novel process for preparing d-α-(6-methoxy-2-naphthyl)propionic acid, which is characterized by hydrolyzing an ester of d-α-(6-methoxy-2-naphthyl)propionic acid in an aqueous alkali (basic) catalyst solution.

DETAILED DESCRIPTION OF THE PREFERRED EMBODIMENTS

The present invention will be described in more detail below.

The ester of d-α-(6-methoxy-2-naphthyl)propionic acid which is used as a starting material may be a lower alkyl ester excluding t-butyl ester of said acid, or an ester of said acid with a phenol group unsubstituted or substituted with an electron attracting group such as Cl, $NO_2$ and Br, preferably methyl ester or ethyl ester, and most preferably methyl ester.

The basic catalyst to be used in this invention includes, for example, an alkali hydroxide such as sodium hydroxide, potassium hydroxide and lithium hydroxide; ammonia; an alkali metal carbonate such as sodium carbonate and potassium carbonate; an alkali metal bicarbonate such as sodium bicarbonate and potassium bicarbonate; an alkali metal salt of an organic acid such as sodium acetate and potassium acetate, a salt of d-α-(6-methoxy-2-naphthyl)propionic acid or α-(6-methoxy-2-naphthyl)propionic acid such as potassium, sodium and ammonium salt of said acid, and the like.

The concentration of the basic catalyst in the aqueous solution may be in the range from 0.01 to 40%, preferably from 0.1 to 25%. The higher the concentration of the solution is, the faster the reaction proceeds.

The reaction temperature may be in the range from 0° C. to a temperature at which the reaction solution is refluxed, i.e., from 0° C. to 100° C.

With respect to the ratio of the ester of d-α-(6-methoxy-2-naphthyl)propionic acid which is used as a starting material to the water which is used as a solvent (ester/water), the smaller the ratio is, the faster the reaction proceeds. On the contrary, the greater the ratio is, the higher the volumetric efficiency is.

The ratio may be usually in the range from 10 to 0.001, preferably 1.0 to 0.001.

The reaction time is not limitative so long as it is enough to carry out the reaction completely and maintains the degree of retention of the configuration in an asymmetric carbon of the product at the desired level or higher. Although the desired reaction time may be varied depending upon the degree of optical purity to be maintained or the concentrations of the catalyst and/or the substrate (ester), it may be usually in the range from approximately 30 minutes to 100 hours. It is possible to shorten or extend the reaction time to any degree depending upon the desired degrees of optical purity and hydrolysis or the reaction conditions.

As the hydrolysis reaction proceeds, an alcohol is produced from the ester group of the starting ester. An aqueous alkali catalyst solution containing the alcohol thus produced or an alcohol in a ratio (by weight or by volume) corresponding to that of the alcohol thus produced is included in the "aqueous alkali catalyst solution" defined in this invention.

The process according to this invention will be described in more detail by the following Examples and Comparative Example.

EXAMPLE 1

1 g of methyl ester of d-α-(6-methoxy-2-naphthyl)-propionic acid ($[\alpha]_D^{25}+78.7°$ (c=1, chloroform); optical purity 100%) suspended in 40 g of 1% aqueous potassium carbonate solution was heated at 100° C. for 6 hours and then cooled. To the resulting reaction mixture, 10 ml of toluene and 5 ml of 5% aqueous sodium hydroxide solution were added to conduct partition. The aqueous layer was neutralized with hydrochloric acid and a solid deposited was extracted with 10 ml of ethyl acetate. After the organic layer was washed with water, concentrated by distilling the solvent away and dried to obtain 0.72 g of white crystal of d-α-(6-methoxy-2-naphthyl)propionic acid. Yield: 76%; $[\alpha]_D^{25}+64.8°$ (c=1.0, Chloroform); optical purity 94%.

COMPARATIVE EXAMPLE 1

(a conventionally available process utilizing alkalicatalyzed hydrolysis).

After 2.3 g of ethyl ester of d-α-(6-methoxy-2-naphthyl)-propionic acid ($[\alpha]_D^{25}+48.6°$; optical purity 100%), 7.3 g of ethanol, 2.5 g of water and 0.5 g of sodium hydroxide were combined, the resulting reaction mixture was heated under reflux for 4 hours, cooled, acidified with hydrochloric acid and thereafter partitioned between water and toluene. The toluene layer thus obtained was washed with water and concentrated to obtain 1.9 g of d-α-(6-methoxy-2-naphthyl)-propionic acid. The optical purity was 45%.

EXAMPLES 2 TO 8

Experiments for Examples 2 to 8 were carried out under the same reaction conditions and post treatment conditions as in Example 1 except that the kinds of the ester of d-α-(6-methoxy-2-naphthyl)propionic acid and the catalyst to be used, reaction time and reaction temperature were varied. The results are shown in the following Table. In the experiments for Examples 2 to 8, used were 1 g of the ester of d-α-(6-methoxy-2-naphthyl)-propionic acid and 40 g of the aqueous alkali catalyst solution.

aqueous solution consisting essentially of water and a basic catalyst.

2. The process according to claim 1, wherein the ester is an ester of said acid with a lower alkanol having 1 to 3 carbon atoms.

3. The process according to claim 2, wherein the lower alkanol is methanol or ethanol.

4. The process according to claim 3, wherein the lower alkanol is methanol.

5. The process according to claim 1, wherein the catalyst is selected from the group consisting of an alkali hydroxide, an alkali metal carbonate, an alkali metal bicarbonate, an alkali metal acetate and a salt of d-α-(6-methoxy-2-naphthyl)propionic acid.

6. The process according to claim 5, wherein the catalyst is sodium hydroxide, potassium hydroxide, sodium carbonate, potassium carbonate, sodium bicarbonate or potassium bicarbonate.

7. The process according to claim 6, wherein the catalyst is sodium carbonate, potassium carbonate, sodium bicarbonate or potassium bicarbonate.

8. The process according to claim 1, wherein the concentration of the catalyst in the aqueous solution is in the range from 0.01 to 40% by weight.

9. The process according to claim 8, wherein the concentration is in the range from 0.1 to 25%.

10. The process according to claim 1, wherein the hydrolysis is carried out at a temperature ranging from 0° C. to 100° C.

11. The process according to claim 2, wherein the catalyst is selected from the group consisting of an alkali hydroxide, an alkali metal carbonate, an alkali metal bicarbonate, an alkali metal acetate and a salt of d-α-(6-methoxy-2-naphthyl)propionic acid; the concentration of the catalyst in the aqueous solution is in the range from 0.01 to 40% by weight; and the hydrolysis is carried out at a temperature ranging from 0° to 100° C.

12. The process according to claim 11, wherein the lower alkanol is methanol or ethanol; the catalyst is sodium hydroxide, potassium hydroxide, sodium carbonate, potassium carbonate, sodium bicarbonate or potassium bicarbonate; and the concentration is in the range from 0.1 to 25% by weight.

13. The process according to claim 12, wherein the lower alkanol is methanol and the catalyst is sodium carbonate, potassium carbonate, sodium bicarbonate or potassium bicarbonate.

TABLE

| Example No. | Ester | Aqueous catalyst Solution | Reaction conditions Temperature (°C.) | Time (hr) | Conversion (%) | Degree of retention of optical activity in carboxylic acid (%) |
|---|---|---|---|---|---|---|
| 2 | Methyl | 0.1% NaOH | 100 | 8 | 25 | 93 |
| 3 | Methyl | 25% NaOH | 20–25 | 6 | 8 | 93 |
| 4 | Methyl | 5% Na$_2$CO$_3$ | 100 | 4 | 99 | 89 |
| 5 | Ethyl | 3% NaHCO$_3$ | 100 | 16 | 31 | 90 |
| 6 | Methyl | 1% NH$_3$ | 100 | 6 | 27 | 91 |
| 7 | Methyl | 1% K$_2$CO$_3$ | 100 | 6 | 76 | 94 |
| 8* | Methyl | 5% K$_2$CO$_3$ | 100 | 7 | 39 | 94 |

*For this Example only, the ester and the aqueous alkali catalyst solution as starting material were used in an amount of 1 g and 4 g, respectively.

We claim:

1. A process for preparing a d-α-(6-methoxy-2-naphthyl)-propionic acid, which comprises hydrolyzing an ester of d-α-(6-methoxy-2-naphthyl)propionic acid in an 14. The process according to claim 13, wherein the ratio of the ester to the water is from 1.0 to 0.001.

15. The process according to claim 1, wherein the ratio of the ester to the water is from 1.0 to 0.001.

* * * * *

UNITED STATES PATENT AND TRADEMARK OFFICE
CERTIFICATE OF CORRECTION

PATENT NO. : 4,611,088

DATED : September 9, 1986

INVENTOR(S) : OHARA et al

It is certified that error appears in the above-identified patent and that said Letters Patent is hereby corrected as shown below:

Title page, under Section [56] References Cited, insert the following:

U.S. PATENT DOCUMENTS -

| | | | |
|---|---|---|---|
| 2,579,021 | 12/1951 | Brezesenska et al | 568/599 |
| 2,616,929 | 11/1953 | Rosen | 568/492 |
| 2,848,500 | 8/1958 | Funck | 568/599 |
| 3,492,356 | 1/1970 | Hall | 568/492 |
| 3,651,148 | 3/1972 | Nelson | 260/606.5B |
| 3,681,432 | 8/1972 | Nelson | |
| 3,828,033 | 8/1974 | Nelson | 260/240 R |
| 4,467,124 | 8/1984 | Kawai et al | 568/842 |

FOREIGN PATENT DOCUMENTS -

2,060,332   6/1971   France

OTHER REFERENCES -

Guthrie, Can. J. Chem., Vol. 53, pp.898-906 (1975).
Middleton et al, J.A.C.S., Vol.86, pp.4948-52 (1964).

Column 1, line 14, change "aromatic" to --racemic--.

UNITED STATES PATENT AND TRADEMARK OFFICE
CERTIFICATE OF CORRECTION

PATENT NO. : 4,611,088                    Page 2 of 2

DATED     : September 9, 1986

INVENTOR(S) : OHARA et al

It is certified that error appears in the above-identified patent and that said Letters Patent is hereby corrected as shown below:

Column 2, line 37, after "40%", insert --by weight--.

Column 4, Claim 9, line 26, after "25%", insert

--by weight--.

Signed and Sealed this

Sixteenth Day of February, 1993

*Attest:*

STEPHEN G. KUNIN

*Attesting Officer*      *Acting Commissioner of Patents and Trademarks*